United States Patent [19]

Hill et al.

[11] Patent Number: 4,698,422
[45] Date of Patent: Oct. 6, 1987

[54] TRIPHOS AND TETRAPHOS GOLD COMPOUNDS AND LIGANDS

[75] Inventors: David T. Hill, North Wales; Randall K. Johnson, Ardmore, both of Pa.

[73] Assignee: SmithKline Beckman Corporation, Philadelphia, Pa.

[21] Appl. No.: 849,078

[22] Filed: Apr. 4, 1986

Related U.S. Application Data

[63] Continuation-in-part of Ser. No. 736,003, May 20, 1985, abandoned.

[51] Int. Cl.⁴ .......................... A61K 31/70; C07H 5/10
[52] U.S. Cl. ................................ 536/17.1; 536/121; 556/14
[58] Field of Search ................. 536/17.1, 121; 556/14; 514/24, 126, 127, 135, 136, 75, 495

[56] References Cited

U.S. PATENT DOCUMENTS

| | | |
|---|---|---|
| 3,364,273 | 1/1968 | Clark et al. |
| 3,445,540 | 5/1969 | Safridis et al. |
| 3,635,945 | 1/1972 | Nemeth et al. ................. 536/17.1 |
| 3,657,298 | 4/1972 | King et al. |
| 4,096,248 | 6/1978 | Lantos ............................ 536/17.1 |
| 4,102,920 | 7/1978 | Bartish |
| 4,115,642 | 9/1978 | Hill et al. ....................... 536/17.1 |
| 4,201,775 | 5/1980 | Filan et al. ..................... 536/17.1 |
| 4,361,707 | 8/1981 | Habib et al. |
| 4,387,087 | 6/1983 | Deutsch et al. |
| 4,645,756 | 2/1987 | Hill et al. |

FOREIGN PATENT DOCUMENTS 0151046  8/1985  European Pat. Off.
0164970 12/1985  European Pat. Off.

OTHER PUBLICATIONS

Shaw et al., *Inorganica Chimica Acta*, 123, 213–216 (1986).
Eggleston et al., *Inorganica Chimica Acta*, 108, 221–226 (1985).
Mirabelli et al., *Biochemical Pharmacology*, 35(9), 1427–1433, 1435–1443 (1986).
Mirabelli et al., *J. Med. Chem.*, 29(2), 218–223 (1986).
Hill et al., Abstract #204, American Chemical Society.
Berners-Price et al., Abstract #244, American Chemical Society.
Mirabelli et al., Abstract #1114, *Proceedings of AACR* 27, Mar. 1986.
Johnson et al., Abstract #1115, *Proceedings of AACR* 27, Mar. 1986.
Hill et al., Abstract #14, 190th American Chemical Society National Meeting.
King et al., *J. Am. Chem. Soc.*, 91 (18), 5191–2 (1969).
King et al., *J. Am. Chem. Soc.*, 93 (17), 4158–66 (1971).
King et al., *Inorg. Chem.*, 10(9), 1861–67 (1971).
King, *Acc. Chem. Res.*, 5, 177–85 (1972).
Antbert et al., *Inorg. Chem.*, 23(5), 4170–4174 (1984).
Cooper et al., *Inorg. Chim. Acta*, 65(5), L185–186 (1982).
Struck et al., *J. Med. Chem.*, 9, 414–416 (1966).
Mirabelli et al., *Proceedings of AACR*, Mar. 1984, No. 1455, p. 367 (1984).
Mirabelli et al., *Cancer Research*, 45, 32–39 (1985).
Johnson et al., *Proceedings of AACR*, Mar. 1985, No. 1001, p. 254 (1985).
Snyder et al., *Proceedings of AACR*, Mar. 1985, No. 1007, p. 255 (1985).
Mirabelli et al., *Proceedings of AACR*, Mar. 1985, No. 1008, p. 256 (1985).

*Primary Examiner*—Ronald W. Griffin
*Attorney, Agent, or Firm*—Carol G. Canter; Edward T. Lentz; Alan D. Lourie

[57] ABSTRACT

Triphos and tetraphos gold compounds which have tumor cell growth-inhibiting activity, pharmaceutical compositions containing an effective, tumor cell growth-inhibiting amount of such a compound or its corresponding triphos or tetraphos ligand, and a method for treating tumor cells sensitive to such a compound or its corresponding triphos or tetraphos ligand.

47 Claims, No Drawings

TRIPHOS AND TETRAPHOS GOLD COMPOUNDS AND LIGANDS

CROSS REFERENCE TO RELATED APPLICATIONS

This application is a continuation-in-part of Ser. No. 736,003 filed May 20, 1985, now abandoned.

BACKGROUND OF THE INVENTION

This invention relates to novel triphos and tetraphos gold compounds which have tumor cell growth-inhibiting activity, pharmaceutical compositions containing an effective tumor cell growth-inhibiting amount of such a novel compound, and a method for treating tumor cells sensitive to such a compound by administering tumor cell growth-inhibiting amounts of such a novel compound to a host animal afflicted by such tumor cells. This invention also relates to novel pharmaceutical compositions comprising an effective, tumor cell growth-inhibiting amount of a triphos or tetraphos ligand, and a method for treating tumor cells sensitive to such ligands by administering tumor cell growth-inhibiting amounts of such ligands to a host animal afflicted by such tumor cells.

Various references including Clark et al., U.S. Pat. No. 3,364,273, issued Jan. 16, 1968; King et al., *J. Am. Chem. Soc.*, 91, (18), 5191-2 (1969); King et al, *J. Am. Chem. Soc.*, 93 (17), 4158-66 (1971); King et al., *Inorg. Chem.*, 10(9), 1851-67 (1971); King, *Acc. Chem. Res.*, 5, 177-85 (1972) and King et al., U.S. Pat. No. 3,657,298, issued Apr. 18, 1982 disclose 1,1,4,7,10,10-hexaphenyl-1,4,7,10-tetraphosphodecane.

Various references including Bartish, U.S. Pat. No. 4,102,920, issued July 25, 1978, and Antberg et al. *Inorg. Chem.*, 23(5), 4170-4174 (1984), disclose bis(2-diphenylphosphinoethyl)phenyl phosphine and/or bis(2-diphenylphosphinopropyl)phenyl phosphine.

Various references including Hebb et al., U.S. Pat. No. 4,361,707 issued Aug. 3, 1981, disclose tris(diphenylphosphinoethyl)phosphine. Deutsch et al., U.S. Pat. No. 4,387,087, issued June 7, 1983, disclose the use of tris(diphenylphosphinoethyl)phosphine in a method of imaging organs with technetium radiopharmaceuticals.

Cooper et al., *Inorg. Chim. Acta*, 65(5), L185-186 (1982), disclose the synthesis and X-ray structure of trichloro-1,1,1-(diphenylphosphinomethyl)ethane[-trigold(I)].

Several references including Hewertson et al., *J. Chem. Soc.*, 1490-1495 (1962) and Safridis et al., U.S. Pat. No. 3,445,540, issued May 20, 1969, disclose μ-[1,1,1-tris(diphenylphosphinomethyl)ethane].

None of the aforementioned references disclose or suggest the compounds, pharmaceutical compositions and/or methods of treatment of subject invention.

SUMMARY OF THE INVENTION

This invention relates to triphos and tetraphos gold(I) compounds of the formula:

$$R-P[A-P-(R)_2]_2;\quad \text{FORMULA (I)}$$
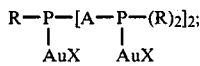

$$P-[A-P-(R)_2]_3;\text{ or}\quad \text{FORMULA (II)}$$
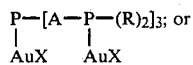

-continued

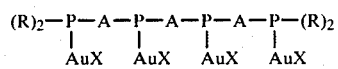   FORMULA (III)

wherein:
R is the same and is phenyl;
A is the same and is a straight or branched alkanediyl chain of from one to six carbon atoms; and
X is the same and is halo or thiosugar.

When X is thiosugar, the attachment of X to the gold atom is through the sulfur atom of the thiosugar.

This invention also relates to a pharmaceutical composition which comprises an effective, tumor cell growth-inhibiting amount of an active ingredient and an inert, pharmaceutically acceptable carrier or diluent, wherein said composition is useful for inhibiting the growth of animal tumor cells sensitive to the active ingredient, and wherein the active ingredient is a compound of Formula (I), Formula (II), Formula (III), or a compound of the formula:

$$[(R)_2-P-CH_2]_3-C-CH_3;\quad \text{FORMULA (IV)}$$
$$|$$
$$AuX$$

$$R-P[A-P-(R)_2]_2;\quad \text{FORMULA (IA)}$$

$$P-[A-P-(R)_2]_3;\quad \text{FORMULA (IIA)}$$

$$\overset{R}{|}\quad\overset{R}{|}\quad\quad \text{FORMULA (IIIA)}$$
$$(R)_2-P-A-P-A-P-A-P-(R)_2;\text{ or}$$

$$[(R)_2-P-CH_2]_3-C-CH_3;\quad \text{FORMULA (IVA)}$$

wherein R, X and A are as defined above.

Another aspect of this invention relates to a method of inhibiting the growth of animal tumor cells sensitive to a compound of Formula (I), Formula (II), Formula (III), Formula (IV), Formula (IA), Formula (IIA), Formula (IIIA) or Formula (IVA) which comprises administering to an animal afflicted with said tumor cells, an effective, tumor cell growth-inhibiting amount of a compound of Formula (I), Formula (II), Formula (III), Formula (IV), Formula (IA), Formula (IIA), Formula (IIIA) or Formula (IVA).

DETAILED DESCRIPTION OF THE INVENTION

By the term "thiosugar" is meant any 1-thioaldose. Examples of such thiosugars include 1-thioglucose, 1-thiogalactose, 1-thiomannose, 1-thioribose, 1-thiomaltose, 1-thiofucose, tetra-O-acetyl-1-thioglucose, tetra-O-acetyl-1-thiomannose, tetra-O-acetyl-1-thiogalactose, tri-O-acetyl-1-thioribose, hepta-O-acetyl-1-thiomaltose and tri-O-acetyl-1-thiofucose.

All the compounds of Formula (I), Formula (II), Formula (III), Formula (IV), Formula (IA), Formula (IIA), Formula (IIIA) and Formula (IVA) are either available commercially or can be prepared by methods available to one skilled in the art.

Generally, the compounds of Formula (I), Formula (II), Formula (III) and Formula (IV) wherein X is chloro can be prepared by reacting the appropriate compound of Formula (IA), Formula (IIA), Formula (IIIA) or Formula (IVA) with chloroauric acid tetrahydrate reduced by treatment with thiodiglycol.

The compounds of Formula (I), (II), (III) and (IV) wherein X is bromo are prepared by reacting the appropriate compounds of Formula (IA), Formula (IIA), Formula (IIIA) or Formula (IVA) with bromoauric acid hydrate, which is commercially available, for example from Strem Chemicals, Inc., Newburyport, Mass., reduced by treatment with thiodiglycol. Alternatively, compounds of Formula (I), (II), (III), and (IV) wherein X is bromo are prepared by treatment of the corresponding compounds of Formula (I), (II), (III) and (IV) wherein X is chloro with sodium bromide in an appropriate non-reactive organic solvent, such as aqueous ethanol or DMF.

The compounds of Formula (I), (II), (III) and (IV) wherein X is iodo are prepared by treatment of the corresponding compounds of Formula (I), (II), (III) and (IV) wherein X is chloro or bromo with sodium iodide in an appropriate non-reactive organic solvent, such as acetone.

All the necessary compounds of Formula (IA), Formula (IIA), Formula (IIIA) or Formula (IVA) are available from commercial sources, for example, Strem Chemicals, Inc., Newburyport, Mass.

To prepare the Formula (I), Formula (II), Formula (III) or Formula (IV) compounds wherein X is thiosugar, the corresponding Formula (I), Formula (II), Formula (III) or Formula (IV) compound wherein X is chloro is reacted with a thiosugar source, for example, sodium thioglucose. The necessary thiosugar source is available from commercial sources, for example, from Sigma Chemicals Co., St. Louis, Mo.

As stated above, the compounds of Formula (I), Formula (II), Formula (III), Formula (IV), Formula (IA), Formula (IIA), Formula (IIIA) and Formula (IVA) have tumor cell growth-inhibiting activity which has been demonstrated in at least one animal tumor model.

P388 lymphocytic leukemia is currently the most widely used animal tumor model for screening for antitumor agents and for detailed evaluation of active compounds. This tumor system is widely accepted as an antitumor agent screening tool because it is sensitive to virtually all of the clinically active antineoplastic agents; quantitative and reproducible; amenable for large-scale screening; and predictive for activity in other animal tumor models. Drugs that are highly active in intraperitoneal (ip) P388 leukemia are generally active in other tumor models as well. The antitumor activity of the compounds of Formula (I), Formula (II), Formula (III), Formula (IV), Formula (IA), Formula (IIA), Formula (IIIA), and Formula (IVA) is demonstrated in the P388 leukemia mouse model employing the following protocol:

$10^6$ P388 leukemia cells are inoculated ip in B6D2F$_1$ mice. Twenty-four hours later, if the tumor inoculum proves to be free of bacterial contamination (as determined by 24 hours incubation in thioglycollate broth), animals are randomized into groups of 6 and housed in shoebox cages. The compound to be evaluated is dissolved in a minimal volume of either N,N-dimethylacetamide (DMA) or 95% ethanol (depending upon solubility). An equal volume of saline is added; if the drug comes out of solution an equal volume of polyethoxylated castor oil is added and then saline qs to a concentration such that the desired dose is delivered in 0.5 ml. The final concentration of DMA, ethanol and polyethoxylated castor oil is $\geq 10$ percent. Dilutions for lower doses are made with saline so there is a decreasing proportion of organic solvents in the vehicle with decreasing dosage. These vehicles provide soluble formulations (or suspensions). Formulations are prepared immediately prior to injection. The compound is administered ip on Days 1 through 5 (i.e. treatment is initiated 24 hrs after tumor inoculation). Each experiment includes three groups of 6 animals as untreated controls and animals treated with a positive control, cisplatin, at two dose levels. Animals are weighed as a group on Days 1, 5 and 9 and average weight change ($\Delta$wt.) is used as a reflection of toxicity. Each experiment also includes an inoculum titration—groups of 8 mice inoculated ip with $10^5$ to $10^9$ P388 leukemia cells. The titration is used to calculate cell kill achieved by treatment with drugs. Animals are monitored daily for mortality and experiments are terminated after 45 days. The endpoint is median survival time (MST) and increase in lifespan (ILS) which is the percentage of increase in MST relative to untreated controls. Untreated controls inoculated ip with $10^6$ P388 leukemia cells generally survive for a median of 9 to 11 days. A drug is considered active if it produces $\geq 25$ percent ILS.

A summary of the evaluation of several compounds of Formula (I), Formula (II), Formula (III), Formula (IV), Formula (IA), Formula (IIA), Formula (IIIA), and Formula (IVA) in the in vivo ip P388 model is shown in the following Table A.

TABLE A

| Structure | Formula |
|---|---|
| R—P[A—P—(R)$_2$]$_2$ with AuX AuX | FORMULA (I) |
| P—[A—P—(R)$_2$]$_3$ with AuX AuX | FORMULA (II) |
| (R$_2$)—P—A—P—A—P—A—P—(R)$_2$ with R, R substituents and AuX AuX AuX AuX | FORMULA (III) |
| [(R)$_2$—P—CH$_2$]$_3$—C—CH$_3$; with AuX | FORMULA (IV) |
| R—P[A—P—(R)$_2$]$_2$; | FORMULA (IA) |
| P—[A—P—(R)$_2$]$_3$; | FORMULA (IIA) |
| (R)$_2$—P—A—P—A—P—A—P—(R)$_2$; or [(R)$_2$—P—CH$_2$]$_3$—C—CH$_3$; with R, R | FORMULA (III) |

| Compound Number | Formula Number | A | X | MTD$^{(a)}$ (mg/kg) | ILS (max)$^{(b)}$ (%) |
|---|---|---|---|---|---|
| 1 | I | (CH$_2$)$_2$ | Cl | 8 | 30/40 |
| 2 | II | (CH$_2$)$_2$ | Cl | 8 | 45/45 |
| 3 | III | (CH$_2$)$_2$ | Cl | 12 | 85/105/50/60/60 |
| 4 | III | (CH$_2$)$_2$ | thioglucose | 8 | 100/55 |
| 5 | IV | N/A | Cl | 20 | 40/30 |
| 6 | IA | (CH$_2$)$_2$ | N/A | 32 | 80/50 |
| 7 | IIA | (CH$_2$)$_2$ | N/A | 64 | 35/30 |
| 8 | IIIA | (CH$_2$)$_2$ | N/A | 64 | 25/40 |
| 9 | IVA | N/A | N/A | 128 | 45/25 |

$^{(a)}$maximally tolerated dose for B6D2F female mice on an ipqDxs regimen.
$^{(b)}$maximum increase in lifespan produced in mice bearing ip P388 leukemia (figures separated by slashes indicate data generated in separate experiments).

Another chemosensitive tumor model is intraperitoneally (ip) implanted M5076 reticulum cell sarcoma in mice. In this system B6D2F female mice are inoculated with 0.5 ml of a 10 percent (w:v) brei of M5076 prepared from pooled subcutaneous (sc) tumors excised at about 21 days from C57B1/6 donors. Drugs are administered ip. Daily treatment is begun 24 hours after implantation and is continued for ten days. The treatment regimen for M5076 is more prolonged than for P388 because of the slower growth rate and longer control survival time of the M5076 tumor. A drug is considered active in this tumor model if it produces ≧25% ILS. The antitumor activity of Compound No. 3 of Table A in the M5076 reticulum cell sarcoma tumore model is set forth in Table B.

TABLE B

| Compound No. [a] | MTD (mg/kg) [b] | ILS (MAX) (%) [c] |
|---|---|---|
| 3 | 8 | 96 |

[a] see Table A for structure.
[b] maximally tolerated dose for B6D2F female mice on an ip qD × 10 regimen.
[c] maximum increase in lifespan produced in mice bearing ip M5076 reticulum cell sarcoma The cytotoxic activity of Compound No. 3 of Table A was evaluated in vivo using B16 melanoma cells. In this system, groups of eight B6D2F$_1$ mice are inoculated ip with 0.5 ml of a 10% (w:v) brei of B15 melanoma prepared from pooled sc tumors excised at 14-21 days from C67B$_1$/6 donor mice. Daily treatment is begun 24 hours after tumor implantation and is continued daily for ten (10) days. The route of drug administration is ip. The mice are monitored daily for survival for sixty (60) days. Antitumor activity is assessed by prolongation of median survival time. An ILS of ≧25% indicates activity in this tumor model.

A summary of the results of the in vivo ip B16 melanoma assay is shown in Table C.

TABLE C

| Compound No. [a] | MTD (mg/kg) [b] | ILS (%) [c] |
|---|---|---|
| 3 | 6 | 30/51 |

[a] see Table A for structure.
[b] maximally tolerated dose for B6D2F$_1$ mice on an ip qD × 10 regimen.
[c] maximum increase in lifespan produced in mice bearing ip B16 melanoma (figures separated by a slash were generated in separate experiments).

The pharmaceutical compositions of this invention comprise an effective tumor cell growth-inhibiting amount of a compound of Formula (I), Formula (II), Formula (III), Formula (IV), Formula (IA), Formula (IIA), Formula (IIIA) or Formula (IVA) and an inert pharmaceutically acceptable carrier or diluent. These compositions are prepared in dosage unit form appropriate for parenteral administration.

Compositions according to the invention for parenteral administration include sterile aqueous or non-aqueous solutions, suspensions or emulsions. The composition may be in the form of a solution of the active ingredient in a minimal volume of dimethylacetamide or ethanol, for example 5% v/v, brought up to volume with peanut oil or normal saline solution. Polyethoxylated castor oil, for example 2 to 5% v/v, may also be used to solubilize the active ingredient. In addition, the composition may be in the form of a slurry with, for example, hydroxypropyl cellulose or other suitable suspending agent. As an emulsifying agent, lecithin for example may be used. The composition may also be provided in the form of a sterile solid which can be dissolved in a sterile injectable medium immediately before use.

Freireich et al., Cancer Chemo. Rept., 50, 219-244 (1966), compared the quantitative toxicity of 18 anticancer drugs in six species after correcting the data to a uniform schedule of treatment for five consecutive days. This analysis demonstrated that mouse, rat, dog, human, monkey and man have essentially the same maximum tolerated dose (MTD) when compared on a basis of mg/m$^2$ of body surface area. The study suggested that Phase I clinical trials could be safely initiated at a dose one-third the animal MTD. The mouse was as useful as any other species in this regard on which to base the calculation. The appropriate therapeutically effective dose for any compound of the invention can therefore be determined readily by those skilled in the art from simple experimentation with laboratory animals, perferably mice.

It will be appreciated that the actual preferred dosages of the compounds of Formula (I), Formula (II), Formula (III), Formula (IV), Formula (IA), Formula (IIA), Formula (IIIA) or Formula (IVA) used in the compositions of this invention will vary according to the particular compound being used, the particular composition formulated, the mode of administration and the particular site, host and disease being treated. The route of internal administration should be selected to ensure that an effective tumor cell growth-inhibiting amount of the compound of Formula (I), Formula (II), Formula l(III), Formula (IV), Formula (IA), Formula (IIA), Formula (IIIA) or Formula (IVA) contacts the tumor. Optimal dosages for a given set of conditions can be ascertained by those skilled in the art using conventional dosage determination tests in view of the above experimental data. For parenteral administration the dose preferably employed is from about 5 to about 1200 mg/m$^2$ of body surface per day for five days, repeated about every fourth week for four courses-of treatment.

The method for inhibiting the growth of animal tumor cells sensitive to a compound of Formula (I), Formula (II), Formula (III), Formula (IV), Formula (IA), Formula (IIA), Formula (IIIA) or Formula (IVA) in accordance with this invention comprises administering to a host animal afflicted with said tumor cells, an effective tumor cell growth-inhibiting amount of a compound of Formula (I), Formula (II), Formula (III), Formula (IV), Formula (IA), Formula (IIA), Formula (IIIA) or Formula (IVA).

EXAMPLES

The following examples illustrate the chemical preparation of several compounds of Formula (I), Formula (II), Formula (III), Formula (IV), Formula (IA), Formula (IIA), Formula (IIIA) and Formula (IVA) which are used in the compositions and methods of this invention and as such are not be be construed as limiting the scope thereof. All temperatures are in degrees Centigrade.

EXAMPLE 1

μ-[Bis(2-diphenylphosphinoethyl)phenylphosphine]-tris(chlorogold)

Chloroauric acid tetrahydrate (2.5 g, 6.07 mmole) in water (10 ml) was reduced upon addition of thiodiglycol (3.0 g, 24.6 mmoles) in water (10 ml)/methanol (60 ml) at 0°. A solution of bis(2-diphenylphosphinoethyl)-phenylphosphine (1.08 g, 2.02 mmole), a Formula (IA)

compound obtained from Strem Chemicals Inc., Newburyport, Mass., in chloroform (50 ml)/methanol (30 ml) was added and the mixture was stirred for several hours, and allowed to come to room temperature. Water was added and the product extracted with chloroform/methylene chloride, dried (MgSO$_4$), filtered and the solvent was removed in vacuo. The residue was slurried with chloroform, diluted with ethanol and the precipitate collected and dried to give 1.75 g (70%) of product, melting point (m.p.) 173°–177°.

EXAMPLE 2

μ-[Tris(2-diphenylphosphinoethyl)phosphine]tetrakis(chlorogold)

Chloroauric acid tetrahydrate (2.5 g, 6.06 mmole) in water (20 ml) was reduced upon addition of thiodiglycol (3.0 g, 24.6 mmole) in water (20 ml)/methanol (60 ml) at 0°. A solution of tris(diphenylphosphinoethyl)phosphine (1.02 g, 1.5 mmole), a Formula (IIA) compound obtained from Strem Chemicals Inc., Newburyport, Mass., in chloroform (30 ml)/methanol (20 ml) was added, and the mixture was stirred for several hours. Water (200 ml) was added, and the mixture was extracted with chdloroform. The chloroform extracts were dried (MgSO$_4$), filtered and the solvent was removed in vacuo. Methanol was added to the residue and the solution was cooled. The crystals were collected, dissolved in methylene chloride, and treated with activated carbon. Then methanol was added and the mixture was cooled. The resulting crystals were collected to give 2.1 g (86%), of the named Formula (II) product, m.p. 181°–3°.

EXAMPLE 3

μ-[1,1,4,7,10,10-Hexaphenyl-1,4,7,10-tetraphosphodecane]tetrakis(chlorogold)

Chloroauric acid tetrahydrate (1.87 g, 4.54 mmol) in water (20 ml) was reduced upon addition of thiodiglycol (3.0 g, 24.6 mmole) in methanol (60 ml)/water (20 ml) at 0°. 1,1,4,7,10,10-hexaphenyl-1,4,7,10-tetraphosphodecane (0.76 g, 1.13 mmole), a Formula (IIIA) compound obtained from Strem Chemicals, Inc. Newburyport, Mass., in chloroform (60 ml)/methanol (20 ml) was added and the mixture was stirred for several hours. The resulting precipitate was collected and dissolved in methylene chloride. Then hexane was added and the mixture was cooled. Collection of successive crops gave 1.35 g (94%) of the named Formula (III) product, m.p. 184°–186°.

EXAMPLE 4

μ-[1,1,4,7,10,10-Hexaphenyl-1,4,7,10-tetraphosphodecane]tetrakis(1-thio-β-D-glucopyranosato-S)gold A mixture of sodium β-D-thioglucose (0.97 g, 4.4 mmoles), obtained from Sigma Chemical Co., St. Louis, Mo., and μ-[1,1,4,7,10,10-Hexaphenyl-1,4,7,10,-tetraphosphodecane]tetrakis(chlorogold) (1.6 g, 1 mmole), prepared as described in Example 3, in methanol (150 ml)/chloroform (150 ml)/water (20 ml) was stirred for 18 hours at ambient temperature, and the solvent was evaporated. The residue was washed with water, and then with acetone. The residue was then treated with boiling methanol and filtered, and the methanol was evaporated. Crystallization of the residue from acetone gave 1.5 g (67%) of the named Formula (III) product, m.p. 267°–272°.

EXAMPLE 5

μ-[1,1,1-Tris(diphenylphosphinomethyl)ethane]tris(chlorogold)

Thiodiglycol (2.0 g, 16.4 mmole) in ethanol (10 ml) was added to chloroauric acid tetrahydrate (1.97 g, 4.8 mmoles) in water (20 ml) kept at 0°. An acetone (8 ml) solution of μ-[1,1,1-Tris(diphenylphosphinomethyl)ethane] (1.0 g, 1.6 mmoles), a Formula (IVA) compound obtained from Strem Chemicals, Inc., Newburyport, Mass., was added and the mixture was stirred overnight. The product was collected, washed with water and recrystallized from dimethylformamide to give 1.1 g of the named Formula (V) product, m.p. 197°–202°. Recrystallization from methylene chloride/ether gave 0.7 g of the named Formula (IV) product, m.p. 205°–210° (dec.).

EXAMPLE 6

Using the procedure of Example 1, by reacting the appropriate Formula (IA) compound and the appropriate haloauric acid tetrahydrate, reduced by treatment with thiodiglycol, the following compounds of Formula (I) wherein X is chloro or bromo are prepared, or by reacting the appropriate Formula (I) compound wherein X is chloro with sodium bromide in an appropriate organic solvent, such as aqueous ethanol or DMF, the following compounds of Formula (I) wherein X is bromo are prepared, and by reacting the appropriate compound of Formula (I) wherein X is chloro or bromo with sodium iodide in an appropriate organic solvent, such as acetone, the following compounds of Formula (I) wherein X is iodo are prepared:

a.  μ-[bis(2-diphenylphosphinomethyl)phenylphosphine]tris(chlorogold)
b.  μ-[bis(2-diphenylphosphinopropyl)phenylphosphine]tris(chlorogold)
c.  μ-[bis(2-diphenylphosphinobutyl)phenylphosphine]tris(chlorogold)
d.  μ-[bis(2-diphenylphosphinopentyl)phenylphosphine]tris(chlorogold)
e.  μ-[bis(2-diphenylphosphinohexyl)phenylphosphine]tris(chlorogold)
f.  μ-[bis(2-diphenylphosphinoethyl)phenylphosphine]tris(bromogold
g.  μ-[bis(2-diphenylphosphinoethyl)phenylphosphine]tris(iodogold)

EXAMPLE 7

Using the procedure of Example 4, by reacting the appropriate thioglucose source with the appropriate Formula (I) compound wherein X is chloro, prepared according to the procedure of Example 1 or 6, the following Formula (I) compounds wherein X is thioglucose are prepared:

a.  μ-[bis(2-diphenylphosphinomethyl)phenylphosphine]tris(1-thio-β-D-glucopyranosato-S)gold
b.  μ-[bis(2-diphenylphosphinoethyl)phenylphosphine]tris(1-thio-β-D-glucopyranosato-S)gold
c.  μ-[bis(2-diphenylphosphinopropyl)phenylphosphine]tris(1-thio-β-D-glucopyranosato-S)gold
d.  μ-[bis(2-diphenylphosphinobutyl)phenylphosphine]tris(1-thio-β-D-glucopyranosato-S)gold
e.  μ-[bis(2-diphenylphosphinopentyl)phenylphosphine]tris(1-thio-β-D-glucopyranosato-S)gold
f.  μ-[bis(2-diphenylphosphinohexyl)phenylphosphine]tris(1-thio-β-D-glucopyranosato-S)gold g. μ-[bis(2-diphenylphosphinoethyl)phenylphosphine]-tris(1-thio-α-D-mannopyranosato-S)gold
h. μ-[bis(2-disphenylphosphinoethyl)phenylphosphine]-tris(1-thio-β-D-galactopyranosato-S)gold
i. μ-[bis(2-diphenylphosphinoethyl)phenylphosphine]-tris(1-thio-D-ribofuranosato-S)gold

EXAMPLE 8

Using the procedure of Example 2, by reacting the appropriate Formula (IIA) compound with the appropriate haloauric aicd tetrahydrate, reduced by treatment with thiodiglycol, the following compounds of Formula (II) wherein X is chloro or bromo are prepared; or by reacting the appropriate Formula (II) compound wherein X is chloro with sodium bromide in an appropriate organic solvent such as aqueous ethanol or DMF, the following compounds of Formula (II) wherein X is bromo are prepared; and by reacting the appropriate Formula (II) compound wherein X is chloro or bromo with sodium iodide in an appropriate organic solvent such as acetone, the following compound of Formula (II) wherein X is iodo are prepared:
a. μ-[Tris(2-diphenylphosphinomethyl)phosphino]tetrakis(chlorogold)
b. μ-[Tris(2-diphenylphosphinopropyl)phosphino]tetrakis(chlorogold)
c. μ-[Tris(2-diphenylphosphinobutyl)phosphino]tetrakis(chlorogold)
d. μ-[Tris(2-diphenylphosphinopentyl)phosphino]tetrakis(chlorogold)
e. μ-[Tris(2-diphenylphosphinohexyl)phosphino]tetrakis(chlorogold)
f. μ-]Tris(2-diphenylphosphinoethyl)phosphino]tetrakis(bromogold)
g. μ-[Tris(2-diphenylphosphinoethyl)phosphino]tetrakis(iodogold)

EXAMPLE 9

Using the procedure of Example 4, by reacting the appropriate thioglucose source with the appropriate Formula (II) compound wherein X is chloro, prepared according to the procedure of Example 2 or 8, the following formula (II) compounds wherein X is thioglucose are prepared:
a. μ-[Tris(2-diphenylphosphinomethyl)phosphine]tetrakis(1-thio-β-D-glucopyranosato-S)gold
b. μ-[Tris(2-diphenylphosphinoethyl)phosphine]tetrakis(1-thio-β-D-glucopyranosato-S)gold
c. μ-[Tris(2-diphenylphosphinopropyl)phosphine]tetrakis(1-thio-β-D-glucopyranosato-S)gold
d. μ-[Tris(2-diphenylphosphinobutyl)phosphine]tetrakis(1-thio-β-D-glucopyranosato-S)gold
e. μ-[Tris(2-diphenylphosphinopentyl)phosphine]tetrakis(1-thio-β-D-glucopyranosato-S)gold
f. μ-[Tris(2-diphenylphosphinohexyl)phosphine]tetrakis(1-thio-β-D-glucopyranosato-S)gold
g. μ-[Tris-(2-diphenylphosphinoethyl)phosphine]tetrakis(1-thio-α-D-mannopyranosato-S)gold
h. μ-[Tris(2-diphenylphosphinoethyl)phosphine]tetrakis(1-thio-β-D-galactopyranosato-S)gold
i. μ-[Tris(2-diphenylphosphinoethyl)phosphine]tetrakis(1-thio-D-ribofuranosato-S)gold

EXAMPLE 10

Using the procedure of Example 3, by reacting the approriate Formula (IIA) compound and the appropriate haloauric acid tetrahydrate, reduced by treatment with thiodiglycol, the following compounds of Formula (III) wherein X is chloro or bromo are prepared; or by reacting the apporpriate compound of Formula (III) wherein X is chloro with sodium bromide in an appropriate organic solvent, such as aqueous ethanol or DMF, the following compounds of Formula (III) wherein X is bromo are prepared; and by reacting the appropriate compound of Formula (III) wherein X is chloro or bromo with sodium iodide in an appropriate organic solvent such as acetone, the following compounds of Formula (III) wherein X is iodo are prepared:
a. μ-[1,1,3,5,7,7-hexaphenyl-1,3,5,7-tetraphosphoheptane]tetrakis(chlorogold)
b. μ-[1,1,5,9,13,13,-hexaphenyl-1,5,9,13-tetraphosphotridecane]tetrakis(chlorogold)
c. μ-[1,1,6,11,16,16-hexaphenyl-1,6,11,16-tetraphosphohexadecane]tetrakis(chlorogold)
d. μ-[1,1,7,13,19,19-hexaphenyl-1,7,13,19-tetraphosphononadecane]tetrakis(chlorogold)
e. μ-[1,1,8,15,22,22-hexaphenyl-1,8,15,22-tetraphosphodocosane]tetrakis(chlorogold)
f. μ-[1,1,4,7,10,10-hexaphenyl-1,4,7,10-tetraphosphodecane]tetrakis(bromogold)
g. μ-[1,1,4,7,10,10-hexaphenyl-1,4,7,10-tetraphosphodecane]tetrakis(iodogold)

EXAMPLE 11

Using the procedure of Example 4, by reacting the appropriate thioglucose source with the appropriate Formula (III) compound wherein X is chloro, prepared according to the procedure of Example 3 or 10, the following Formula (III) compounds wherein X is thioglucose are prepared:
a. μ-[1,1,3,5,7,7-hexaphenyl-1,3,5,7-tetraphosphoheptane]tetrakis(1-thio-β-D-glucopyranosato-S)gold
b. μ-[1,1,5,9,13,13-hexaphenyl-1,5,9,13-tetraphosphotridecane]tetrakis(1-thio-β-D-glucopyranosato-S)gold
c. μ-[1,1,6,11,16,16-hexaphenyl-1,6,11,16-tetraphosphohexadecane]tetrakis(1-thio-β-D-glucopyranosato-S)gold
d. μ-[1,1,7,13,19,19-hexaphenyl-1,7,13,19-tetraphosphononadecane]tetrakis(1-thio-β-D-glucopyranosato-S)gold
e. μ-[1,1,8,15,22,22-hexaphenyl-1,8,15,22-tetraphosphodocosane]tetrakis(1-thio-β-D-glucopyranosato-S)gold
f. μ-[1,1,4,7,10,10-hexaphenyl-1,4,7,10-tetraphosphodecane]tetrakis(1-thio-β-D-galactopyranosato-S)gold
g. μ-[1,1,4,7,10,10-hexaphenyl-1,4,7,10-tetraphosphodecane]tetrakis(1-thio-D-mannopyranosato-S)gold
h. μ-[1,1,4,7,10,10-hexaphenyl-1,4,7,10-tetraphosphodecane]tetrakis(1-thio-D-ribofuranosato-S)gold

EXAMPLE 12

Using the procedure of Example 5, by reacting the appropriate Formula (IVA) compound with the appropriate haloauric acid tetrahydrate, reduced by treatment with thiodiglycol, the following compounds of Formula (IV) wherein X is bromo or chloro are prepared; or by reacting the apporpriate compound of Formula (IV) wherein X is chloro with sodium bromide in an appropriate organic solvent, such as aqueous ethanol or DMF, the following compounds of Formula (IV) wherein X is bromo are prepared; and by reacting the appropriate compound of Formula (IV) wherein X is chloro or bromo with sodium iodide in an appropriate organic solvent such as acetone, the following compounds of Formula (IV) wherein X is iodo are prepared:
a. μ-[1,1,1-tris(diphenylphosphinomethyl)ethane]tris(bromogold)
b. μ-[1,1,1-tris(diphenylphosphinomethyl)ethane]tris(iodogold)

EXAMPLE 13

Using the procedure of Example 4, by reacting the appropriate thioglucose source with the named compound of Example 5, the following Formula (IV) compounds wherein X is thioglucose are prepared:
a. μ-[1,1,1-tris(diphenylphosphinomethyl)ethane]tris(1-thio-β-D-glucopyranosato-S)gold
b. μ-[1,1,1-tris(diphenylphosphinomethyl)ethane]tris(1-thio-β-D-galactopyranosato-S)gold
c. μ-[1,1,1-tris-diphenylphosphinomethyl)ethane]tris(1-thio-α-D-mannopyranosato-S)gold
d. μ-[1,1,1-tris(diphenylphosphinomethyl)ethane]tris(1-thio-D-ribofuranosato-S)gold

EXAMPLE 14

As a specific embodiment of a composition of this invention, an active ingredient, such as one part of the compound of Example 3, is dissolved in 5 parts of dimethylacetamide and 5 parts of polyethoxylated castor oil and then normal saline solution qs, and is administered parenterally in one dose of 15 mg/m² to a host animal afflicted with tumor cells sensitive to that compound.

What is claimed is:

1. A compound of the formula:

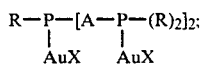  FORMULA (I)

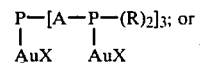  FORMULA (II)

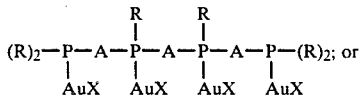  FORMULA (III)

wherein:
R is phenyl;
A is a straight or branched alkanediyl chain of from one to six carbon atoms; and
X is halo or thiosugar.

2. The compound of claim 1 which is a compound of Formula (I).

3. The compound of claim 2 which is μ-[bis(2-diphenylphosphinoethyl)phenylphosphine]tris(chlorogold).

4. The compound of claim 1 which is a compound of Formula (II).

5. The compound of claim 4 which is μ-[tris(2-diphenylphosphinoethyl)phosphine]tetrakis(chlorogold).

6. The compound of claim 1 which is a compound of Formula (III).

7. The compound of claim 6 which is μ-[1,1,4,7,10,10-hexaphenyl-1,4,7,10-tetraphosphodecane]tetrakis(chlorogold).

8. The compound of claim 6 which is μ-[1,1,4,7,10,10-hexaphenyl-1,4,7,10-tetraphosphodecane]tetrakis(1-thio-β-D-glucopyranosato-S)gold.

9. A pharmaceutical composition which comprises an effective tumor cell growth inhibiting amount of an active ingredient and an inert, pharmaeutically acceptable carrier or diluent, wherein said composition is useful for inhibiting the growth of animal tumor cells sensitive to the active ingredient, and wherein the active ingredient is a compound of the formula:

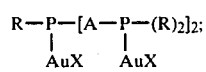  FORMULA (I)

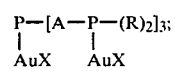  FORMULA (II)

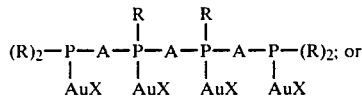  FORMULA (III)

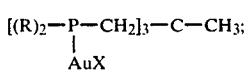  FORMULA (IV)

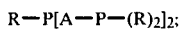  FORMULA (IA)

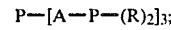  FORMULA (IIA)

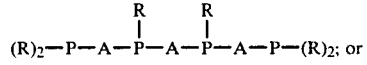  FORMULA (IIIA)

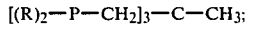  FORMULA (IVA)

wherein:
R is phenyl;
A is a straight or branched alkanediyl chain of from one to six carbon atoms; and
X is halo or thiosugar.

10. The composition of claim 9 wherein the active ingredient is a compound of Formula (I).

11. The composition of claim 10 wherein the compound is μ-[bis(2-diphenylphosphinoethyl)phenylphosphine]tris(chlorogold).

12. The composition of claim 9 wherein the active ingredient is a compound of Formula (II).

13. The composition of claim 12 wherein the compound is μ-[tris(2-diphenylphosphinoethyl)tetrakis(chlorogold).

14. The composition of claim 9 wherein the active ingredient is a compound of Formula (III).

15. The composition of claim 14 wherein the compound is μ-[1,1,4,7,10,10-hexaphenyl-1,4,7,10-tetraphosphodecane]tetrakis(chlorogold).

16. The composition of claim 14 wherein the compound is μ-[1,1,4,7,10,10-hexapenyl-1,4,7,10-tetraphosphodecane]tetrakis(1-thio-β-D-glucopyranosato-S)gold.

17. The composition of claim 9 wherein the active ingredient is a compound of Formula (IV).

18. The composition of claim 17 wherein the compound is μ-[1,1,1-tris(diphenylphosphinomethyl)ethane]tris(chlorogold).

19. The composition of claim 9 wherein the active ingredient is a compound of Formula (IA).

20. The composition of claim 19 wherein the compound is bis(2-diphenylphosphinoethyl)phenylphosphine.

21. The composition of claim 9 wherein the active ingredient is a compound of Formula (IIA).

22. The composition of claim 21 wherein the compound is tris(diphenylphosphinoethyl)phosphine.

23. The composition of claim 9 wherein the active ingredient is a compound of Formula (IIIA).

24. The composition of claim 23 wherein the compound is 1,1,4,7,10,10-hexaphenyl-1,4,7,10-tetraphosphodecane.

25. The composition of claim 9 wherein the active ingredient is a compound of Formula (IVA).

26. The composition of claim 26 wherein the compound is -[1,1,1-tris(diphenylphosphinomethyl)ethane].

27. The composition of claim 9 wherein the composition is in a dosage unit form adapted for parenteral administration.

28. The composition of claim 27 wherein the parenteral dosage unit is adapted to administer from about 5 to about 1200 mg/m² of body surface.

29. A method of inhibiting the growth of animal tumor cells sensitive to a compound of the formula:

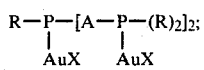  FORMULA (I)

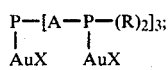  FORMULA (II)

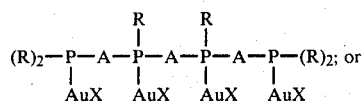  FORMULA (III)

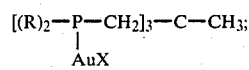  FORMULA (IV)

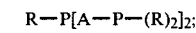  FORMULA (IA)

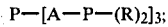  FORMULA (IIA)

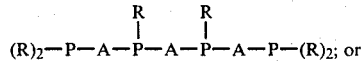  FORMULA (IIIA)

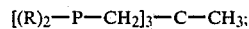  FORMULA (IVA)

wherein:
R is phenyl;
A is a straight or branched alkanediyl chain of from one to six carbon atoms; and
X is halo or thiosugar, which comprises administering to an animal afflicted with said tumor cells, an effective, tumor cell growth-inhibiting amount of said compound.

30. The method according to claim 29 wherein the compound is a compound of Formula (I).

31. The method according to claim 30 wherein the compound is μ-[bis(2-diphenylphosphinoethyl)phenylphosphino]tris(chlorogold).

32. The method according to claim 29 wherein the compound is a compound of Formula (II).

33. The method according to claim 32 wherein the compound is μ-[tris(2-diphenylphosphinoethyl)phosphine]tetrakis(chlorogold).

34. The method according to claim 29 wherein the compound is a compound of Formula (III).

35. The method according to claim 34 wherein the compound is μ-[1,1,4,7,10,10-hexaphenyl-1,4,7,10-tetraphosphodecane]tetrakis(chlorogold).

36. The method according to claim 29 wherein the compound is a compound of Formula (IV).

37. The method according to claim 36 wherein the compound is μ-[1,1,1-tris(diphenylphosphinomethyl)ethane]tris(chlorogold).

38. The method according to claim 29 wherein the compound is a compound of Formula (IA).

39. The method according to claim 38 wherein the compound is bis(2-diphenylphosphinoethyl)phenylphosphine.

40. The method according to claim 29 wherein the compound is a compound of Formula (IIA).

41. The method according to claim 40 wherein the compound is tris(diphenylphosphinoethyl)phosphine.

42. The method according to claim 29 wherein the compound is a compound of Formula (IIIA).

43. The method according to claim 42 wherein the compound is 1,1,4,7,10,10-hexaphenyl-1,4,7,10-tetraphosphodecane.

44. The method according to claim 29 wherein the compound is a compound of Formula (IVA).

45. The method according to claim 44 wherein the compound is μ-[1,1,1-tris(diphenylphosphinomethyl)ethane].

46. The method according to claim 29 wherein the administration is parenteral and the amount is selected from a unit dose range of from about 5 to about 1200 mg/m² of body surface administered per dose for five days.

47. The method according to claim 47 wherein the administration is repeated about every fourth week for four courses of treatment.

* * * * *

UNITED STATES PATENT OFFICE
CERTIFICATE OF CORRECTION

PATENT NO. : 4,698,422

DATED : October 6, 1987

INVENTOR(S) : David T. Hill and Randall K. Johnson

It is certified that error appears in the above-identified patent and that said Letters Patent are hereby corrected as shown below:

In claim 47 at column 14, line 47, delete "claim 47" and insert -- claim 46 -- therefor Signed and Sealed this Eighth Day of March, 1988

*Attest:*

DONALD J. QUIGG

*Attesting Officer*  *Commissioner of Patents and Trademarks*